US006956645B2

(12) United States Patent
Wittman et al.

(10) Patent No.: US 6,956,645 B2
(45) Date of Patent: Oct. 18, 2005

(54) APPARATUS AND METHOD FOR IN-SITU MEASUREMENT OF POLYMER QUANTITIES OUTPUT FROM AN EXTRACTOR

(75) Inventors: Georg Wittman, Herzogenaurach (DE); Joerg Blaessing, Oberkochen (DE); Matthias Stoessel, Mannheim (DE); Jan Birnstock, Leipzig (DE); Karsten Heuser, Erlangen (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 277 days.

(21) Appl. No.: 10/327,031

(22) Filed: Dec. 20, 2002

(65) Prior Publication Data

US 2004/0036856 A1 Feb. 26, 2004

(30) Foreign Application Priority Data

Dec. 21, 2001 (DE) ......................................... 101 63 463

(51) Int. Cl.$^7$ ................................................. G01J 3/00
(52) U.S. Cl. ...................................... 356/300; 356/317
(58) Field of Search ........................ 356/300, 317–318; 250/458.1–461.2; 347/19

(56) References Cited

U.S. PATENT DOCUMENTS

| | | |
|---|---|---|
| 3,653,767 A | 4/1972 | Liskowitz |
| 4,651,011 A | 3/1987 | Ors et al. |
| 4,751,517 A * | 6/1988 | Crean et al. .................. 347/19 |
| 5,434,430 A * | 7/1995 | Stewart ........................ 347/19 |
| 6,087,196 A * | 7/2000 | Sturm et al. .................. 438/29 |
| 6,305,777 B1 * | 10/2001 | Lee .............................. 347/19 |
| 6,624,434 B1 * | 9/2003 | Shen et al. .................. 250/573 |
| 2002/0089561 A1 * | 7/2002 | Weitzel et al. ................ 347/19 |

FOREIGN PATENT DOCUMENTS

| | | |
|---|---|---|
| DE | 19754459 A1 | 6/1999 |
| EP | 0 733 896 A2 | 9/1996 |
| EP | 0892028 A2 | 7/1998 |

OTHER PUBLICATIONS

Lampert, M.A. et al., "Current Injection on Solids", 1970, Academic Press, pp. 1–13, 84–156 and 305–326.

Pardo, D.A. et al., "Application of Screen Printing in the Fabrication of Organic Light–Emitting Devices", Sep. 1, 2000, Advanced Materials, 12, No. 17, pp. 1249–1252.

* cited by examiner

Primary Examiner—F. L. Evans
Assistant Examiner—Kara Geisel
(74) Attorney, Agent, or Firm—Fish & Richardson P.C.

(57) ABSTRACT

Apparatus and procedure for the in situ measurement of quantities of polymer printed onto supports A source of radiation 2 sends electromagnetic radiation onto a droplet 9, 10 of polymer solution or polymer dispersion, which is printed onto a support 4. A detector 3 measures the transmitted or re-emitted radiation. Controlled by a comparator device 6 and a control unit 5, the printing parameters are corrected in situ, if necessary. In this manner, a controlled adjustment of the layer thickness of organic light-emitting diodes and therefore luminosity and color perception can be achieved.

38 Claims, 4 Drawing Sheets

APPARATUS AND METHOD FOR IN-SITU MEASUREMENT OF POLYMER QUANTITIES OUTPUT FROM AN EXTRACTOR

Apparatus and procedure for the in situ measurement of quantities of polymer imprinted onto supports.

The invention relates to an apparatus and the applicable procedure for measuring in situ the droplet size of imprinted quantities of polymer, in the manufacture of organic LED displays.

Organic light-emitting diodes (OLEDs) are becoming increasingly important in optoelectronics.

OLEDs belonging to two basic technologies. Some OLEDs are made on the basis of monomers while others are based on polymers.

Since the electroluminescence in the OLEDs polymer layers has a strongly non-linear relationship with the layer thickness of the polymer (because the current density is a strongly non-linear function of that layer thickness), it is essential in the OLED manufacturing process to ensure the production of a polymer layer whose thickness is as constant as possible over the OLEDs surface. It is only in this fashion that luminosity and color perception of the OLEDs can be adjusted in a manner that will meet the predetermined specifications. In fact, the existence of substrate points not covered by polymer may even cause a short circuit between cathode and anode, causing the loss of functionality of the entire OLED display.

It is true that the thickness of the polymer layer on the substrate can be precisely adjusted by means of area-wide coating procedures such as spin-coating methods. However, because of the requirement that this be followed by a structuring with its consequent high expenses, this process is not preferred in OLED manufacture.

In order to maintain the structures of the polymer on the substrate it is consequently advantageous to imprint upon the substrate, with the aid of a printing process, an already structured polymer solution.

When using printing processes such as inkjet printing or screen printing it is critical for obtaining the desired result that the quantity of polymer to be imprinted be measured with great accuracy.

In the past, the setting of the measuring could only be adjusted by checking the resulting printing after the fact—which meant high OLED losses if the printing process was defective. Furthermore, attempts to correct (by means of a second printing pass) layers found in a post-process check to be insufficiently thick, resulted in the creation of an additional boundary surface between the first layer (which conventionally had already started to dry) and the fresh second layer—a boundary surface that could have a deleterious effect on the electrical and optical properties of the light-emitting diodes.

What is more, a second printing pass meant additional expenditures of time and money. The task of the invention is to overcome the disadvantages of the state of the art. In particular, the object is to create an apparatus, which will make it possible to regulate, in situ, the printing run and with it the print result—i.e., to directly check the quality of the polymer layer during the printing process, modifying or correcting it if necessary.

According to the invention, this task is achieved in that a printing machine—preferably of a conventional type for printing organic LED's—is equipped with a source of radiation and a detector. A specific optical property of the polymer is used for the purpose of measuring the quantities of polymer.

The procedures, which are suitable for such measurements, comprise absorption spectroscopy, fluorescence analysis, polarimetry and ellipsometry.

In a preferred variant, the electromagnetic radiation emitted by the polymer is measured, taking advantage of the absorption of the radiation in the visible or near-ultraviolet range of the spectrum.

When using this absorptive capacity, in principle one of two methods of measurement can be used:

The radiation absorption of the printed droplet can be determined, on the one hand, by inserting the detector into the beam path, behind the droplet. The quantity of transmitted radiation is recorded there. The larger the quantity of polymer in the droplet, the higher will be the absorption of the radiation.

Conversely, the measurement can be effected in a reflective mode, where both the source of radiation and the detector are arranged on the same side of the substrate, at an appropriate reflection angle to each another. As the quantity of polymer in the droplet increases, the absorption is greater and the reflection correspondingly lower.

Both methods of measuring absorption (by transmission and by reflection) can also be used so as to supplement one another. This has the advantage of permitting speedier detection and correction of measurement errors.

In another preferred variant, the optical activity of the polymer is put to use—i.e., its capability of rotating the plane of vibration of linearly polarized light. This property is used in procedures such as polarimetry and ellipsometry.

As is the case in absorption spectroscopy, the measurements can be carried out either in a reflection mode, in which the source of the radiation and the detector are located on the same side of the substrate, at an appropriate reflection angle to one another; or else the measurement is taken in the transmission mode, where the detector is inserted in the beam path, behind the droplet.

The quantity of polymer that is traversed by the radiation affects the change in the polarization of the radiation. Absolute quantities as well as phase relationships of the electromagnetic radiation can change while traversing the polymer. In both variants of this procedure the source of radiation must emit polarized light and the detector must be able to determine the change in polarization.

The source of radiation can radiate linearly, circularly or elliptically polarized light.

In another, especially preferred variant, the radiation emitted by the polymer is measured by using the fluorescent properties of the polymer materials. The polymers used in the active layer in organic light-emitting diodes specifically possess the property of fluorescence; consequently it makes sense to take advantage of this particular property in order to determine the magnitude of the printed droplet, hence the thickness of the active layers.

In so doing, a detector records the radiation re-emitted by the polymer, the detector being located at any desired angle to the radiation-source/droplet line.

Regardless of whether the optical property of the polymer that is utilized is its absorptive capacity or its fluorescent capacity, the actual value of the amount of radiation, recorded by the detector, is compared in a control device with a predetermined specified value. If there is a deviation between the actual value and the specified value, a control device connected behind the detector immediately corrects parameters of the printing process such as droplet size and droplet print frequency.

Since optical methods of measurement operate using measuring times on the order of microseconds or less, while a typical printing process for individual display areas lies in the order of milliseconds, deviations from the desired printing result are recorded even before the print head has moved away from the defectively imprinted location. Consequently the print result can be corrected by a repeat imprinting, without causing the formation of a boundary layer between the first and the second print layer.

More importantly, however, in addition to repairing a previously imprinted point it is also possible to correct the printing parameters for the further course of the print run.

In a preferred variant the imprinted layer is measured immediately after the impact of a droplet and, if necessary, the printing process is modified for the following printing stage.

In another variant, the droplets are already measured while still in flight between print head and substrate. In so doing, the quantity of polymer contained in the droplet is equivalent to the quantity that impacts the support.

In many printing processes, such as inkjet printing, it is critical to achieve a precise relative positioning of the print head with respect to the substrate. Frequently this is done by means of a procedure in which a test pattern is printed in an unused area of the substrate. The position of this test pattern in relation to specific markings on the substrate is then determined with the aid of an optical measurement system located close to the print head and is then used to calibrate the coordinates. This procedure requires a suitable light source that preferably can also be used for the in situ analysis of the quantity of polymer. This saves extra weight on the print head, as well as space and expenses.

Below we shall explain in greater detail the apparatus and the procedure according to the invention, using four embodiments with the FIGS. 1 through 4.

Figure 1:
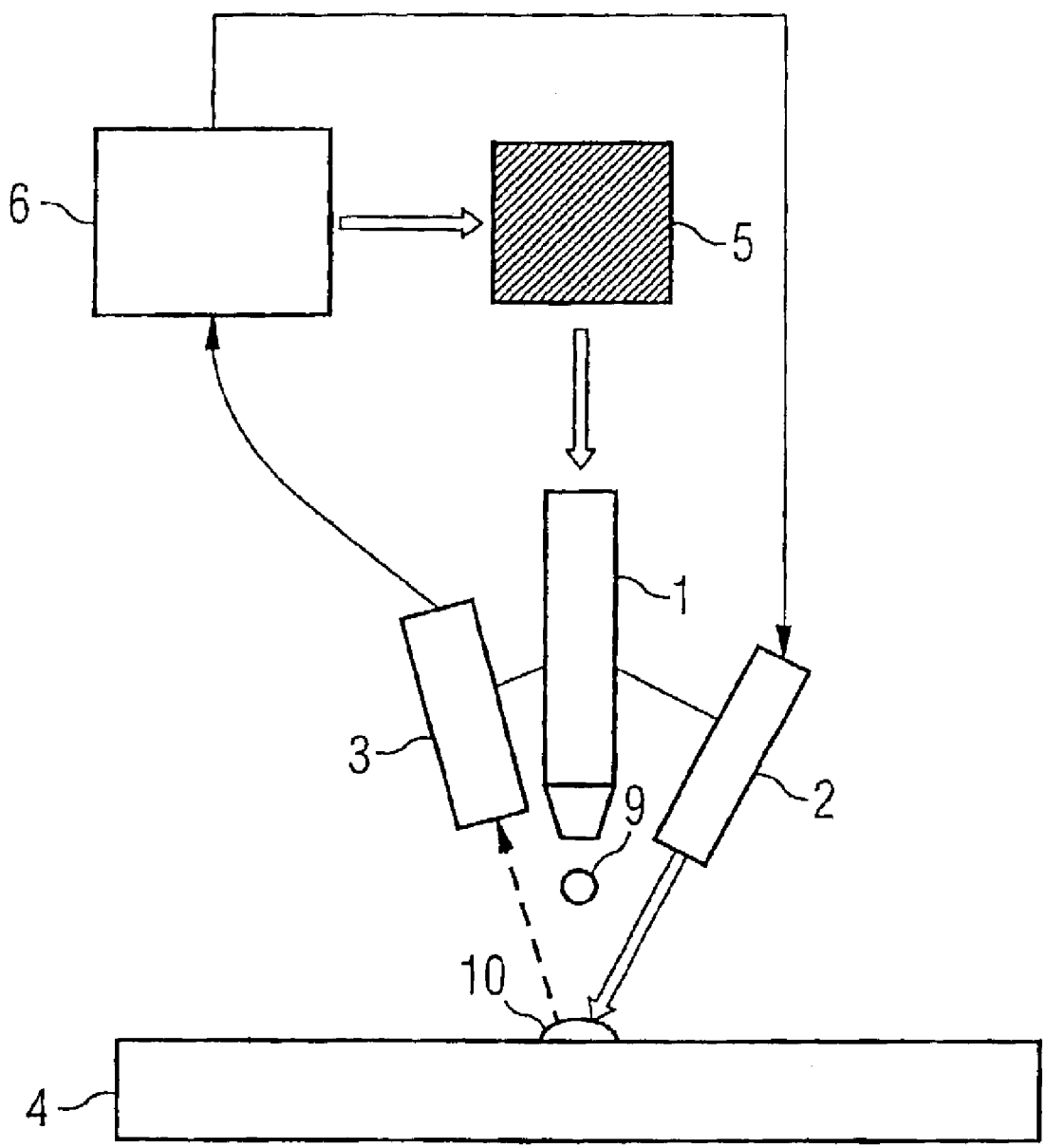
FIG. 1 shows a schematic representation of the first embodiment of an apparatus according to the invention.
Figure 2:
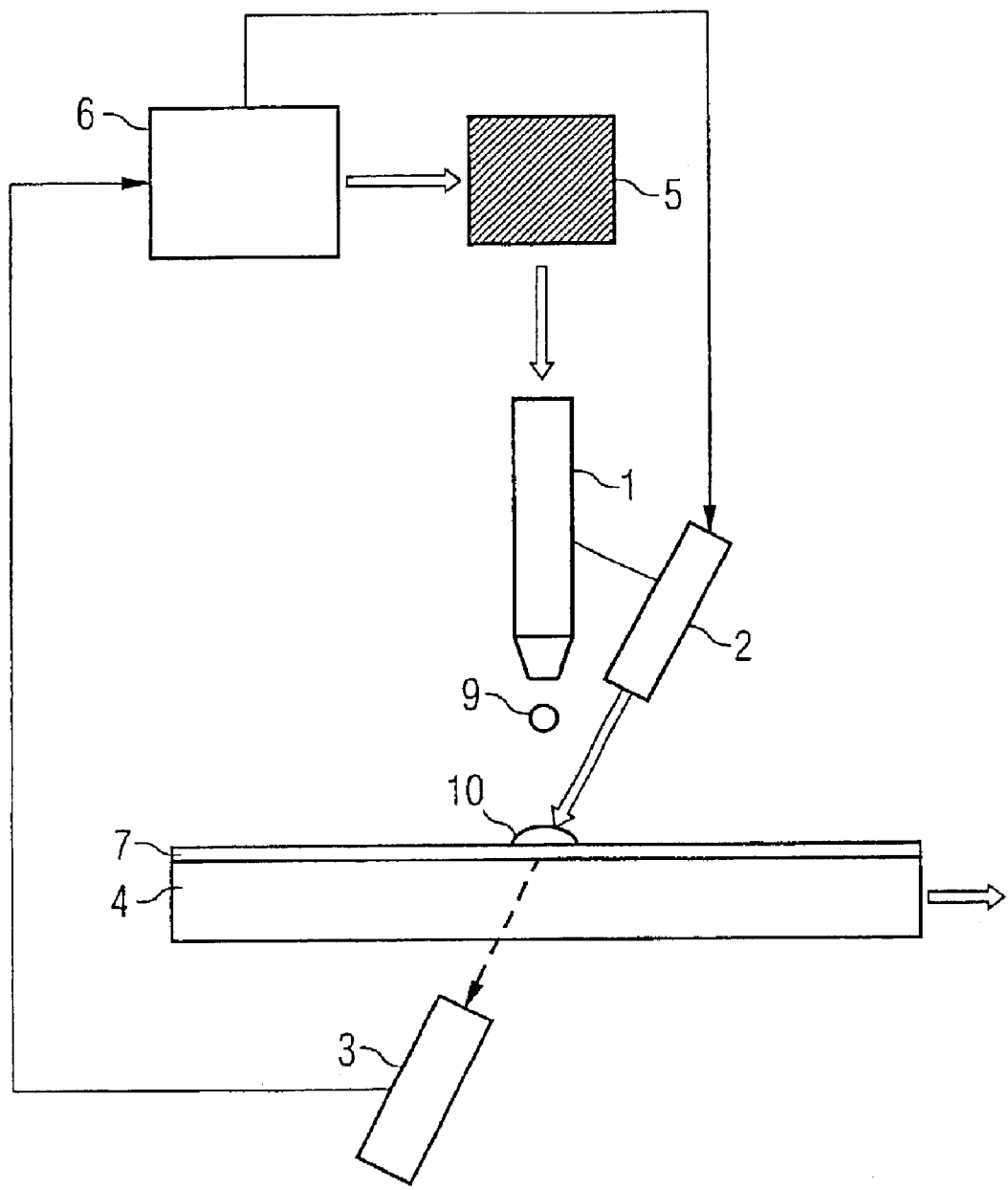
FIG. 2 shows a schematic representation of the second embodiment of an apparatus according to the invention.
Figure 3:
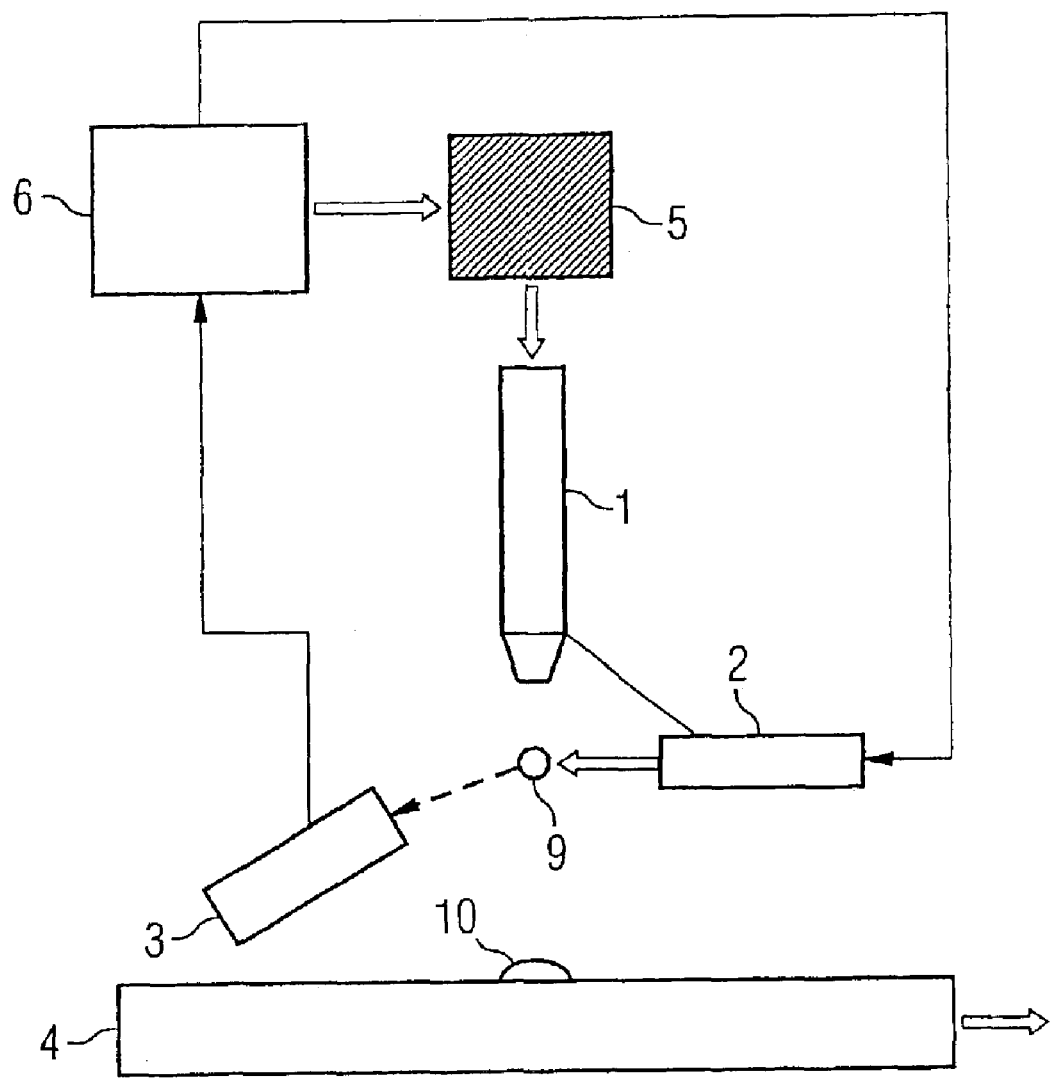
FIG. 3 shows a schematic representation of the third embodiment of an apparatus according to the invention.
Figure 4:
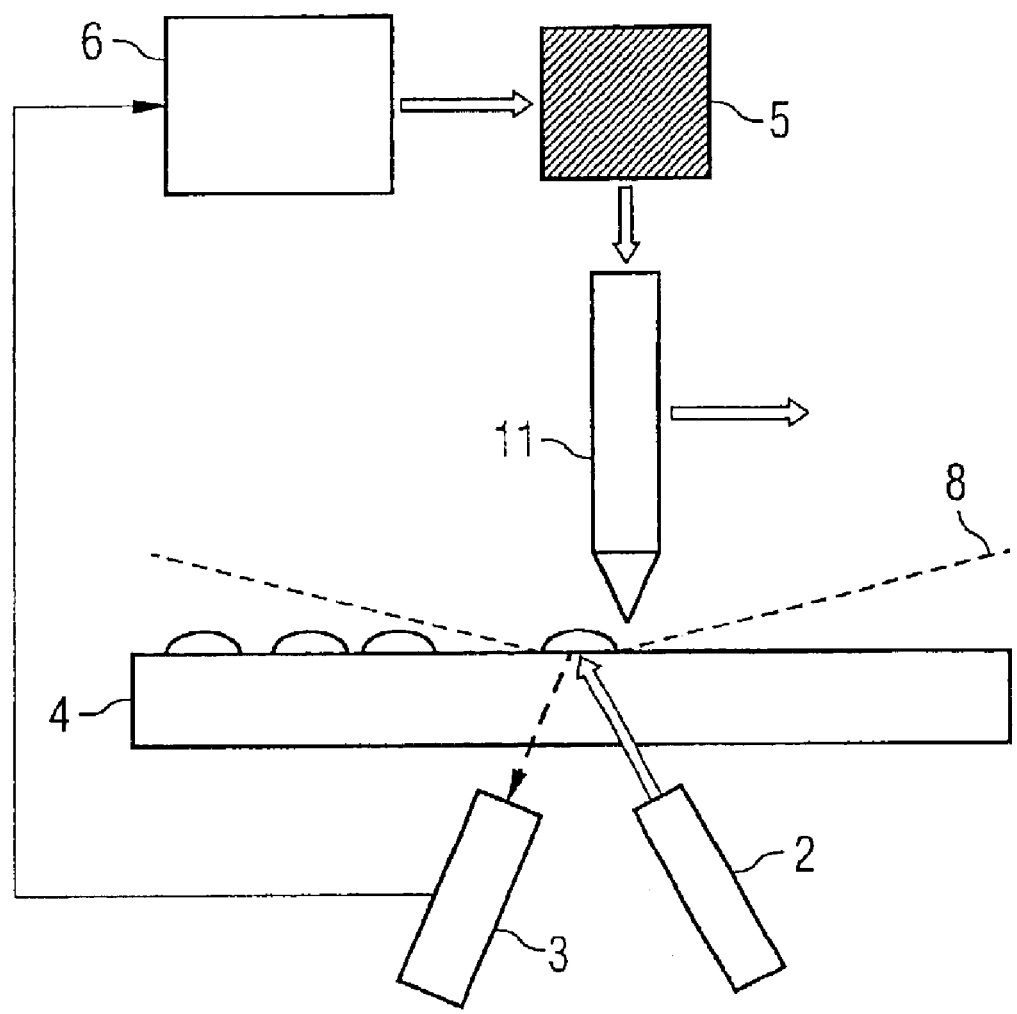
FIG. 4 shows a schematic representation of the fourth embodiment of an apparatus according to the invention.

EMBODIMENT 1 (FIG. 1):

This involves a measuring apparatus for the droplet regulation of a polymer droplet imprinted onto a substrate, by using the droplet's fluorescent properties.

The printing apparatus in this example is an inkjet print head 1 using piezo technology, with which a glass substrate 4 can be imprinted with a solution of an electroluminescent polymer. Laterally to print head 1 there is a source of radiation 2 with a radiation that is coordinated with the absorptive characteristics of the polymer. A primary radiation emitted by the source of radiation 2 is focused essentially on the impact area of the droplet onto the substrate 4. Closely after the moment of impact on substrate 4 a fluorescence process is stimulated in droplet 10 by means of said primary radiation. The secondary photons thus generated are processed in the optical condenser of a detection device 3 located next to the print head 1, and are detected and quantified with a fluorescence detector of the detection device 3. The information thus obtained provides insight into the volume of the droplet on the glass substrate. This information is further processed in an electronic comparator device 6 and, by comparing it with a specified value, is used for the direct control of droplet volume in an electronic control board 5 of the print head 1, as well as to provide fault analysis.

The arrangement of the first embodiment, described above in connection with FIG. 1, can also be operated in reflection mode, in which the polymer droplet is not made to fluoresce but where merely a radiation reflected by the drop of polymer is detected. In this mode the quantity of absorbed radiation is determined in order to find the quantity of imprinted polymer.

Still in the reflection mode, the arrangement of the first embodiment as described in connection with FIG. 1 can also be used to determine the quantity of imprinted polymer with the use of polarimetry or ellipsometry, via the effect of the in-radiated polarized light.

EMBODIMENT 2 (FIG. 2):

This involves a measuring apparatus for the droplet regulation of a polymer droplet imprinted onto a substrate with electrode, by using its absorptive properties.

In this example the printing apparatus is an inkjet print head 1 using bubble jet technology, with which a transparent substrate can be imprinted according to embodiment 1; in the example a glass substrate 4 is equipped with a transparent electrode 7, such as, for instance, an indium/tin oxide electrode. In lieu of a fluorescent radiation as used in the first embodiment, in this construction a radiation transmitted through the droplet 10 and the substrate 4 is detected, by means of a detection device 3, and then uses it for in situ control of the droplet parameters.

Alternatively this arrangement can be used, utilizing an appropriate radiation, to detect a radiation emitted from the polymer droplet 10 by means of fluorescence.

Furthermore the same arrangement can be used, utilizing polarized radiation, to detect the change in the polarization caused by the polymer droplet 10.

EMBODIMENT 3 (FIG. 3):

This involves a measuring apparatus for the droplet regulation of an in-flight droplet of polymer, by using its fluorescent properties.

In this example the printing apparatus is an inkjet print head 1 with which a transparent substrate 4 can be imprinted according to embodiment 1. As in example 1, there occurs the detection of the fluorescent radiation of a droplet, except that in this case the detection involves a droplet 9 that is still in flight. By means of a detector 3, which is arranged at any desired angle to the axis of the primary radiation, the equipment detects the fluorescent radiation and uses it to control droplet parameters.

Alternatively an arrangement can be used as in this embodiment to take advantage of the absorption characteristics of the polymer, using an appropriate radiation to measure radiation transmitted through the droplet, if detector 3 is arranged, say, on the beam axis of the source of radiation 2.

Furthermore in the same embodiment, using a polarized radiation, a radiation transmitted through the droplet can be measured with respect to the change in polarization, if the detector 3 is arranged, say, on the beam axis of the source of radiation 2.

EMBODIMENT 4 (FIG. 4):

This involves a measuring apparatus for the regulation of the process of printing a polymer layer via screen printing onto a support, using the polymer's fluorescent properties.

In this example the printing apparatus is a screen printing machine with which a polymer solution can be applied onto a substrate 4 from a structured screen 8 and a squeegee 11. By means of a primary-radiation source 2 and a detector 3 for the fluorescent radiation below the substrate 4, the layer thickness of the polymer film is detected through the transparent substrate 4. Via a control device, this information is used to control the squeegee parameters of the screen-printing installation (contact pressure, velocity, etc.), thus effecting the in situ control of the layer thickness.

Alternatively, this arrangement according to this embodiment can be used to measure the change in the radiation characteristics relative to the polarization, if the primary-radiation source 2 emits polarized light and the detector 3 can measure the polarization characteristics.

Obviously the procedure according to the invention is not limited to the embodiments specifically described here, but rather extends to all apparatus and procedures that possess the defining features of the invention.

Above mentioned print-run monitoring procedure can also be advantageously used when imprinting other supports such as paper, textures, glass, ceramics, and metal. The transmission mode cannot be used with non-transparent materials.

In addition to polymer solutions all other color-printing systems can be subjected to optical in situ measurement during printing, as described above, provided they feature an optical property such as absorptivity, fluorescing capacity or optical activity.

What is claimed is:

1. An apparatus for measuring an optical property of a quantity of polymer applied by a printing device onto a support and correcting the quantity of polymer applied, comprising:
   a source of radiation to irradiate a droplet of polymer solution or polymer dispersion during a printing process, the source including at least a primary beam;
   a detector of radiation, which is arranged in relation to both the source of radiation and the droplet in such a way that the detector receives either radiation re-emitted by the droplet or radiation transmitted through the droplet at a time at which the droplet is capable of being imprinted with a subsequent droplet and before a boundary surface forms between the droplet and the subsequent droplet; and
   a control unit configured to cause a printing device to print the subsequent droplet when the detector detects the droplet as having less than a desired quantity of polymer, wherein the subsequent droplet is printed on the droplet before the boundary surface forms.

2. The apparatus according to claim 1, wherein the optical property is fluorescing capacity.

3. The apparatus according to claim 1, wherein the optical property is absorptivity in the visible or near-ultraviolet range of the spectrum.

4. The apparatus according to claim 1, wherein the optical property is optical activity.

5. The apparatus according to claim 1, further comprising a comparator device, and wherein the detector is configured to measure a property of the radiation and generates a value, and the comparator device compares the value as received from the detector with a predetermined specified value.

6. The apparatus according to claim 5 wherein the optical property comprises a polarization of the radiation.

7. The apparatus according to claim 5 wherein the optical property comprises a quantity of the radiation.

8. The apparatus according to claim 5, wherein the control unit is coupled to the comparator device and is directly or indirectly coupled with the printing device, if there is a deviation between the actual value and the specified value, the control unit corrects at least one printing parameter of the printing device.

9. The apparatus according to claim 1, wherein the source and the detector are arranged so that the droplet is measured before the droplet is on the support.

10. The apparatus according to claim 9, wherein the droplet is measured on a path from the printing device to the support.

11. The apparatus according to claim 1, wherein the detector is arranged on an axis of the primary beam of the source to receive transmitted radiation.

12. The apparatus arcording to claim 1, wherein the detector is arranged within a reflection angle of the primary beam of the source reflected on the support to receive reflected radiation.

13. The apparatus accoording to claim 1, wherein the detector is arranged to rcceive emitted radiation.

14. An apparatus for measuring an optical property of a quantity of polymer applied by a printing device onto a support, comprising:
   a source of radiation to irradiate a droplet of polymer solution or polymer dispersion during a printing process, the source including at least a primary beam; and
   a detector of radiation, which is arranged in relation to both the source of radiation and the droplet in such a way that the detector receives either radiation re-emitted by the droplet or radiation transmitted through the droplet at a time at which the droplet is capable of being imprinted with a subsequent droplet and before a boundary surface forms between the droplet and the subsequent droplet;
   wherein the source and the detector are arranged so that the droplet is measured when the droplet is on the support.

15. A system for measuring an optical property of a quantity of polymer applied by a printing device onto a support and correcting the quantity of polymer applied, comprising:
   a support;
   a printing device for printing the quantity of polymer onto the support wherein the printing device can print a droplet of polymer solution or polymer dispersion;
   a source of radiation, operable to irradiate the droplet, with at least a primary beam, during a printing process;
   a detector of radiation, operable to receive either radiation re-emitted by the droplet or radiation transmitted through the droplet at a time at which the droplet is capable of being imprinted with a subsequent droplet and before a boundary surface forms between the droplet and the subsequent droplet; and
   a control unit configured to cause the printing device to print the subsequent droplet when the detector detects the droplet as being below a desired quantity of polymer, wherein the subsequent droplet is printed on the droplet before the boundary surface forms.

16. The system according to claim 15, wherein the support is a substrate for at least one organic light-emitting diode.

17. The system according to claim 15, wherein the printing device is an inkjet print head with piezo technology or bubble jet technology.

18. The system according to claim 17, wherein the printing device is a screen-printing unit.

19. The system according to claim 15, wherein the printing device is a printing device for a relief printing process, a photogravure printing process, an offset printing process, a pad printing process, or a stencil printing process.

20. The apparatus according to claim 15, wherein the source of radiation is the same source that is used in an organic light-emitting diode manufacturing process with an optical recognition system.

21. A method for measuring an optical property of a quantity of polymer applied by a printing device onto a support and correcting the quantity of polymer applied, comprising:

printing a droplet of polymer solution or polymer dispersion onto the support;

irradiating the droplet with electromagnetic radiation during the printing process;

detecting, during the printing process, radiation that is transmitted through, reflected from, or re-emitted by the droplet;

determining whether the droplet has less than a desired quantity of polymer; and if the droplet has less than the desired quantity of polymer, printing a subsequent droplet on the droplet before a boundary surface forms on the droplet.

22. A method according to claim 21, wherein the optical property is fluorescing capacity.

23. A method according to claim 21, wherein the optical property is absorptivity in the visible or near-ultraviolet range.

24. A method according to claim 21, wherein the optical property is optical activity.

25. The method according to claim 21, further comprising comparing an actual value of the radiation detected to a predetermined specified value to determine if there is a deviation between the actual value and the predetermined specified value.

26. The method according to claim 25, further comprising changing at least one printing parameter on the printing device when there is a deviation between the actual value and the predetermined specified value.

27. The method according to claim 21, wherein the droplet is measured at a point in time closely after the droplet impacts upon the support.

28. the method according to claim 21, wherein the droplet is measured on a path from the printing device to the support, before the droplet impacts the support.

29. The method according to claim 21 wherein the detecting step includes receiving transmitted radiation.

30. The method according to claim 29, wherein the detecting step is performed by a detector arranged on an axis of a primary beam of the source on a side of the droplet opposite to the source.

31. The method according to claim 21, wherein the detecting step includes receiving reflected radiation.

32. The method according to claim 31, wherein the detecting step is performed by a detector arranged within a reflection angle of a primary beam of a source reflected on the support.

33. The method according to claim 21 wherein the detecting step includes receiving radiation emitted by the droplet by fluorescence.

34. The method according to claim 21 wherein the support is a substrate of an organic light-emitting diode.

35. The method according to claim 21 wherein a printing device is used to print the droplet and the printing device is an inkjet print head which is capable of operating with piezo technology or bubble jet technology.

36. The method according to claim 21 wherein a printing device is used to print the droplet and the printing device is a screen-printing unit.

37. The method according to claim 21 wherein a printing device is used to print the droplet and the printing device is a printing device for a relief printing process, a photogravute printing process, an offset printing process, a pad printing process, or a stencil printing process.

38. The method according to claim 21 wherein a source of radiation is used to irradiate the droplet and the source that is used is a source used in an optical light-emitting diode manufacturing process in an optical recognition system.

* * * * *

UNITED STATES PATENT AND TRADEMARK OFFICE
CERTIFICATE OF CORRECTION

PATENT NO. : 6,956,645 B2
DATED : October 18, 2005
INVENTOR(S) : Georg Wittman et al.

It is certified that error appears in the above-identified patent and that said Letters Patent is hereby corrected as shown below:

Title page,
Item [56], References Cited, OTHER PUBLICATIONS,
replace "Lampert, M.A. et. al., "Current Injection on Solids", 1970," with
-- Lampert, M.A. et. al., "Current Injection in Solids", 1970 --.

Column 6,
Line 13, replace "arcording" with -- according --.
Line 17, replace "accoording" with -- according --.
Line 18, replace "rcceive" with -- receive --.

Column 8,
Line 4, replace "the method" with -- The method --.
Line 33, replace "photogravute" with -- photogravure --.

Signed and Sealed this

Fourth Day of April, 2006

JON W. DUDAS
*Director of the United States Patent and Trademark Office*